United States Patent [19]

Deinhammer et al.

[11] 4,201,715
[45] May 6, 1980

[54] PROCESS FOR THE ANILIDIZATION OF CARBOXYLIC ACID ESTERS

[75] Inventors: Wolfgang Deinhammer; Hellmuth Spes, both of Burghausen, Fed. Rep. of Germany

[73] Assignee: Wacker-Chemie GmbH, Munich, Fed. Rep. of Germany

[21] Appl. No.: 962,352

[22] Filed: Nov. 20, 1978

[30] Foreign Application Priority Data

Jan. 5, 1978 [DE] Fed. Rep. of Germany ....... 2800506

[51] Int. Cl.² ............................................ C07D 309/32
[52] U.S. Cl. ............................. 260/345.7 R; 546/316;
260/347.3; 260/557 R; 260/558 R; 549/72
[58] Field of Search ...................... 260/347.3, 332.2 C,
260/345.7 R, 557 R, 558 R; 546/316

[56] References Cited

U.S. PATENT DOCUMENTS

| 3,978,091 | 8/1976 | Tsuchiya et al. | 260/347.3 |
| 4,094,990 | 6/1978 | Hubele | 260/347.3 |

OTHER PUBLICATIONS

Migrdichian "Organic Synthesis" vol. 2 (1957) p. 1439.

*Primary Examiner*—Alan L. Rotman
*Assistant Examiner*—R. W. Ramsuer
*Attorney, Agent, or Firm*—Allison C. Collard; Thomas M. Galgano

[57] ABSTRACT

Process for the anilidization of carboxylic acid esters of the general formula $R_1COOR_2$, wherein $R_1$ is a cycloaliphatic or substituted cycloaliphatic radical with 3-8 C-atoms, preferably 5-6 C-atoms, an aromatic or substituted aromatic radical, preferably a heterocyclic or substituted heterocyclic radical, more particularly an oxygen-containing heterocyclic radical, with 4-5 C-atoms, and $R_2$ is a hydrocarbon radical with up to 4 C-atoms, preferably 1-2 C-atoms, wherein such esters are reacted in the presence of aniline with equimolar amounts of magnesium dianilide and/or aluminum trianilide in the fluid phase. The products obtained are used as intermediates or directly as pesticides.

6 Claims, No Drawings

PROCESS FOR THE ANILIDIZATION OF CARBOXYLIC ACID ESTERS

The invention relates to the anilidization of carboxylic acid esters.

The direct reaction of carboxylic acid esters with aniline often does not lead to products of economical yields and purity. The anilidization by means of sodium anilide requires the technically problematic handling with sodium or sodium hydride, respectively. A modification of this process with an attempt to obtain carboxylic acid anilides from carboxylic acid esters and halogenmagnesium anilide has the shortcoming, that Grignard reactions have to be resorted to on a technical scale. Moreover, per mol reaction product, 2 mols of a Grignard compound have to be used.

It is the object of the present invention to provide a process which avoids the shortcomings of the known art, which is simpler and leads to higher yields; also the reaction products obtained by this method are easier to deal with in processing.

According to the invention, this can be achieved by reacting a compound of the general formula $R_1COOR_2$, wherein $R_1$ is a cycloaliphatic or substituted cycloaliphatic radical with 3–8 C-atoms, preferably 5–6 C-atoms, an aromatic or substituted aromatic radical, preferably a heterocyclic or substituted heterocyclic radical, more particularly an oxygen-containing heterocyclic radical with 4–5 C-atoms, wherein the substituting groups may be alkyl up to 4 C-atoms, or may be up to two more carboxylic groups, $R_2$ is a hydrocarbon radical with up to 4 C-atoms, especially 1–2 C-atoms, in the presence of aniline with equimolar amounts of magnesium dianilide and/or aluminum trianilide in fluid phase.

It is advantageous to operate with a 20-fold molar excess of aniline, calculated on the carboxylic acid ester. Sometimes, it may be desirable to use organic solvents in the reaction mixture.

It is surprising that in the reaction carried out according to the invention, a higher yield is obtained with a purity of the reaction product of more than 96% by weight, so that further purification, e.g., by recrystallization, is dispensable. This is all the more surprising, since the operator skilled in the art would have expected, from the publication of Lazier and Atkins, J. Am. Chem. Society, 46, pp.741–743, that the magnesium or aluminum alkoholate formed in the reaction would result in an alkylated anilide difficult to remove. Furthermore, the process according to the invention enables the operator to obtain anilidization of carboxylic acid esters hitherto hard to produce with the conventional method.

The preparation of the metal anilides to be used according to the invention is carried out by heating a mixture of metal and aniline. In this process, the metal is used in the form of shavings which are activated, e.g., by the presence of small amounts of a mercury salt. When an excess of aniline is present, the metal anilide is produced in the form of a solution or suspension.

The carboxylic acid ester is introduced into the solution or suspension by mixing it thereinto. The ensuing heating of the reaction mixture requires, at times, that the mixture be cooled. Subsequent to the main reaction, it is desirable to let the mixture stand at the reaction temperature for at least 10 minutes and up to 24 hours. The temperature of the reaction, which is carried out at normal pressure, may be 20°–180° C., the preferred temperature being 50°–140° C. The amount of carboxylic ester added is equimolar, calculated on the metal anilide. When several carboxylic ester groups are present in a single molecule, a corresponding amount of aniline has to be used. It is, of course, possible to add to the reaction mixture an inert hydrocarbon, e.g., benzene, toluene, xylene, cyclohexane, or an ether, such a diethyl ether, diisopropyl ether, dibutyl ether and the like. Preferably, however, the reaction is made to proceed exclusively in the excess amount of aniline present from the metal anilide formation. The removal of excessive aniline after the reaction does not present any difficulties. In view of its low boiling point as compared to the carboxylic acid anilide, the major amount of aniline is removed by distillation, preferably at reduced pressure. The remaining mixture can be worked up with water, with formation of alcohol, carboxylic acid anilide, and metal hydroxide. Mineral acid, preferably hydrochloric or sulfuric acid, is used for acidification, and the carboxylic anilide insoluble in the aqueous medium, is filtered off. A manner of modified work-up consists of dissolving the anilide in organic solvents (if desired when heating) which provide a phase separation with water, adding water to the solvent, acidifying with mineral acid and processing the organic phase after separation from the aqueous phase. The remaining residue may be recrystallized. However, the purity of the product is usually so high that it may be directly used in commerce.

Examples of compounds which can be produced by the process according to the invention are the following:

1. Aromatic Anilide, e.g., 2-Methylbenzanilide or 1, 3, 5-Benzenetricarboxylic acid anilide;

2. Saturated mononuclear cycloaliphatic Anilides as well as simple unsaturated mononuclear cycloaliphatic Anilides, e.g., 2-Methyl-cyclohex-1-ene-1 carboxanilide;

3. Saturated or partially unsaturated heterocyclic systems, 2, 3-Dihydro-4H-thiopyrananilides, e.g., 2-Methyl-5, 6-dihydro-4H-thiopyran-3-carboxanilide, Dihydro-p-dioxinailides, as well as 2, 3-Dihydro-1,4-oxathilnanilide, preferably 2, 3-Dihydrofurananilide, 2, 3-Dihydro-4H-pyrananilide, especially 2-Methyl-4, 5-dihydrofuran-3-carboxanilide, 2-Methyl-5, 6-dihydro-4H-pyran-3-carboxanilide.

4. Unsaturated (aromatic) heterocyclic Anilides, e.g., Thiophen-2-carboxanilide, 2-Methyl-thiophen-3-carboxanilide, 2-Methylpyridine-3-carboxanilide or 2, 6-Dimethyl-pyridine-3, 5-dicarboxanilide, preferably containing the Furan ring, particularly 2-Methylfuran-3-carboxanilide or 2, 5-Dimethyl-3-furan-carboxanilide or 2,4,5-Trimethyl-furan-3-carboxanilide.

The products obtained according to the invention may be used as intermediates. Some of them are valuable plant protective agents.

Example 1

1,3,5-Benzene carboxylic anilide.

2.7 g Al-shavings were etched with aqueous Hg II $Cl_2$-solution, then shortly washed with water, methanol, toluene and aniline, and finally refluxed with 80 ml aniline for 5 hours, while hydrogen was escaping. At 90° C., 11.35 g 1,3,5-Benzene-tricarboxylicmethyl ester were added dropwise within 10 minutes and stirred for 4 hours. The mixture was cooled, and then poured, while stirring, into an excess of 10% hydrochloric acid, one portion at a time. The precipitate forming was drawn off, washed to neutrality, and dried: Obtained 17.6 g of 1,3,5-benzene carboxylic anilide, Fp (from ethanol) 319°–321° C.

Example 2

25 g magnesium shavings, 0.1 g sodium hydride (80% in white oil) and 600 ml aniline were refluxed for 7 hours in the absence of oxygen from the air, with hydrogen escaping; then the mixture was cooled to 120° C. and within a period of 20 minutes 140 g 2-methyl-furan-3-carboxylic methyl ester were added dropwise while stirring. After stirring for 2 hours at 110°–120° C., the excess of aniline was distilled off in vacuo. The remaining melt was dissolved in 400 mol toluene at 80° C. Thereupon, 100 ml water and 350 ml 30% hydrochloric acid were added at 60°–80° C. The aqueous bottom layer was separated and can be recovered for the aniline dissolved as hydrochloride and used further, after alkalinization.

The toluene solution was shaken twice more with 5% hydrochloric acid at 60°–80° C., and then twice with water, and yielded after removal of toluene by evaporation, 196 g 2-methyl-3-furan carboxylic anilide of 98% purity.

Example 3

2,5-dimethyl-3-furan-carboxylic anilide.

Similarly to Example 2, the above anilide was obtained from 25 g magnesium shavings in 600 ml aniline and 168 g 2,5-dimethyl-3-furan carboxylic ethyl ester in an amount of 208 g, and a purity 97.5%.

Examples 4 to 7

The following anilides were prepared in accordance with Example 2 from 1 mol magnesium and 1 mol carboxylic ethyl ester with yields of 95–98% and with purities of 96 to 98%:

Examples 4 to 7

Example 4: 2-Thiophen carboxanilide
Example 5: 2-Methyl-4, 5-dihydrofuran-3-carboxanilide
Example 6: 2-Methyl-5, 6-dihydro-4H-pyran-3-carboxanilide
Example 7: 2-Methyl-cyclohexo-1-ene-1-carboxanilide

Example 8

To 0.1 mol magnesium anilide in 100 ml aniline, were added drop by drop 12.5 g 2,6-dimethyl-3, 5-pyridine dicarboxylic ethyl ester within 5 minutes and stirred for 5 hours at 110° C. To the reaction mixture, 500 ml water were added and concentrated hydrochloric acid was used for acidification to pH 2, while stirring. The precipitate formed was then drawn off, washed to neutrality, and dried; Obtained: 17.5 g 2,6-dimethyl-pyridine-3, 5-dicarboxylic anilide.

The anilides prepared according to Examples 1–8 correspond to their physical properties completely to the preparations made according to known methods.

The above examples are given by way of illustration and not of limitation. According to the invention, the anilidization of carboxylic esters is carried out with magnesium di- and aluminum tri-anilides. The advantage of the process according to the invention as compared to those known from the art can be seen in the easier accessability of the anilidization means, the higher yields and purity of the products obtained, which makes them immediately applicable for further use in commerce.

What is claimed is:

1. A process for the anilidization of carboxylic acid esters of the general formula $R_1COOR_2$, which comprises reacting in fluid phase such esters in which $R_1$ is selected from the group consisting of cycloaliphatic radicals and substituted cycloaliphatic radicals having from 3–8 C-atoms, aromatic and substituted aromatic radicals, heterocyclic and substituted heterocyclic radicals, and $R_2$ is a hydrocarbon radical with up to 4-atoms, in the presence of aniline with equimolar amounts of magnesium dianilide, aluminum trianilide, or a mixture of the two anilides.

2. The process according to claim 1, wherein the cycloaliphatic radical $R_1$ contains 5–6 C-atoms.

3. The process according to claim 1, wherein the aromatic radical $R_1$ is a heterocyclic radical.

4. The process according to claim 1, wherein the aromatic radical $R_1$ is an oxygen-containing heterocyclic radical with 4–5 C-atoms, having as substituents alkyl groups with up to 4 C-atoms and up to two more carboxylic radicals.

5. The process according to claim 1, wherein the hydrocarbon radical $R_2$ has 1–2 C-atoms.

6. The process according to claim 1, wherein the reaction is carried out at normal pressure in the prescence of up to a 20-fold excess of aniline, calculated on the carboxylic ester.

* * * * *

UNITED STATES PATENT AND TRADEMARK OFFICE
CERTIFICATE OF CORRECTION

PATENT NO. : 4,201,715
DATED : May 6, 1980
INVENTOR(S) : WOLFGANG DEINHAMMER

It is certified that error appears in the above—identified patent and that said Letters Patent is hereby corrected as shown below:

Column 1, line 45, change "the"(second occurence) to --this--. Column 2, line 43, change "Dihydro-p-dioxinailides" to --Dihydro-p-dioxinanilides--. Column 4, line 13, change "to" to --in--.

Signed and Sealed this

Twelfth Day of August 1980

[SEAL]

Attest:

SIDNEY A. DIAMOND

Attesting Officer

Commissioner of Patents and Trademark